(12) United States Patent
van Mechelen et al.

(10) Patent No.: US 10,684,229 B2
(45) Date of Patent: Jun. 16, 2020

(54) OPTICAL SENSING SYSTEM FOR DETERMINING HYDROGEN PARTIAL PRESSURE

(71) Applicant: ABB Schweiz AG, Baden (CH)

(72) Inventors: Jacobus Ludevicus Martinus van Mechelen, Regensdorf (CH); Robin Gremaud, Zürich (CH); Ruud Johannes Westerwaal, Barsingerhorn (NL); Bernard Dam, The Hague (NL)

(73) Assignee: ABB Schweiz AG, Baden (CH)

( * ) Notice: Subject to any disclaimer, the term of this patent is extended or adjusted under 35 U.S.C. 154(b) by 258 days.

(21) Appl. No.: 15/816,717

(22) Filed: Nov. 17, 2017

(65) Prior Publication Data

US 2018/0095041 A1 Apr. 5, 2018

Related U.S. Application Data

(63) Continuation of application No. PCT/EP2016/060805, filed on May 13, 2016.

(30) Foreign Application Priority Data

May 18, 2015 (EP) ..................................... 15167999

(51) Int. Cl.
*G01N 21/77* (2006.01)
*G01N 33/28* (2006.01)
(Continued)

(52) U.S. Cl.
CPC ..... *G01N 21/7703* (2013.01); *G01N 21/8507* (2013.01); *G01N 33/2841* (2013.01);
(Continued)

(58) Field of Classification Search
CPC ........ G01N 21/77; G01N 33/28; H01F 27/12; H01F 27/40
(Continued)

(56) References Cited

U.S. PATENT DOCUMENTS 4,661,320 A * 4/1987 Ito ........................ G01N 21/783
250/226
5,783,152 A 7/1998 Nave
(Continued)

FOREIGN PATENT DOCUMENTS

JP 2011-85576 * 4/2011
WO 2007049965 A1 5/2007

OTHER PUBLICATIONS

Butler, M. A., Journal of the Electrochemical Society 1991, 138, L46-L47.*
(Continued)

*Primary Examiner* — Arlen Soderquist
(74) *Attorney, Agent, or Firm* — Taft Stettinius & Hollister LLP; J. Bruce Schelkopf

(57) ABSTRACT

An optical sensing system for sensing hydrogen in a fluid comprising a first optical sensor comprising a first optical fiber, wherein an end portion of the first optical fiber is coated with a first hydrogen-sensitive multilayer on an end surface perpendicular to a longitudinal axis of the first optical fiber, the first multilayer being adapted to change its optical properties dependent on a hydrogen partial pressure in the fluid and dependent on a temperature of the fluid, with a known first characteristic; a second optical sensor comprising a second optical fiber, wherein an end portion of the second optical fiber is coated with a second hydrogen-sensitive multilayer on an end surface perpendicular to the longitudinal axis of the second optical fiber, the second multilayer being adapted to change its optical properties dependent on the hydrogen partial pressure in the fluid and dependent on a temperature of the fluid, with a known second characteristic which is different from the first characteristic; at least one light source adapted for coupling light into the first optical fiber and the second optical fiber, at least one light detector adapted for detecting light reflected by the
(Continued)

first and second multilayer, a control unit adapted for calculating the hydrogen partial pressure in the fluid by using the first characteristic and the second characteristic and an output signal of the at least one light detector.

13 Claims, 4 Drawing Sheets

(51) Int. Cl.
 H01F 27/12 (2006.01)
 H01F 27/40 (2006.01)
 G01N 21/85 (2006.01)
(52) U.S. Cl.
 CPC .......... *H01F 27/12* (2013.01); *H01F 27/402* (2013.01); *G01N 2021/772* (2013.01); *G01N 2021/7773* (2013.01); *G01N 2021/8528* (2013.01); *H01F 2027/406* (2013.01)
(58) Field of Classification Search
 USPC .................................................. 436/60, 144
 See application file for complete search history.

(56) References Cited

U.S. PATENT DOCUMENTS

| | | | |
|---|---|---|---|
| 6,535,658 B1 | 3/2003 | Mendoza et al. | |
| 2002/0017126 A1* | 2/2002 | DiMeo, Jr. | G01N 21/59 73/31.05 |
| 2005/0118064 A1 | 6/2005 | Berg | |
| 2005/0169807 A1* | 8/2005 | Carpenter | G01N 21/783 436/144 |
| 2008/0291452 A1* | 11/2008 | Dam | G01N 33/005 356/437 |
| 2009/0084161 A1* | 4/2009 | Wienecke | G01N 21/783 73/31.05 |
| 2009/0135425 A1* | 5/2009 | Uchiyama | G01M 3/20 356/437 |
| 2009/0210168 A1 | 8/2009 | Vincelette et al. | |
| 2010/0054999 A1* | 3/2010 | Uchiyama | G01N 21/7703 422/91 |
| 2014/0158877 A1 | 6/2014 | Wysocki et al. | |
| 2014/0374578 A1 | 12/2014 | Bertrand et al. | |
| 2015/0063418 A1 | 3/2015 | Wysocki et al. | |

OTHER PUBLICATIONS

Van der Sluis, P. et al, Applied Physics Letters 1997, 70, 3356-3358.*
Benson, D. K. et al, SPIE 1999, 3535, 185-202.*
Richardson, T. J. et al, Applied Physics Letters 2002, 80, 1349-1351.*
Bodzenta, J. et al, Sensors and Actuators B 2002, 87, 82-87.*
Borgschulte, A. et al, Applied Surface Science 2006, 253, 1417-1423.*
Pasturel, M. et al, Applied Physics Letters 2006, 89, paper 021913, 3 pages.*
Slaman, M. et al, Sensors and Actuators B 2007, 123, 538-545.*
Dam, B. et al, Scripta Materialia 2007, 56, 853-858.*
Maciak, E. et al, Thin Solid Films 2007, 515, 8351-8355.*
Slaman, M. et al, International Journal of Hydrogen Energy 2008, 33, 1084-1089.*
Qu, J. et al, International Journal of Hydrogen Energy 2009, 34, 1910-1915.*
Palmisano, V. et al, International Journal of Hydrogen Energy 2010, 35, 12574-12578.*
Gautam, Y. K. et al, International Journal of Hydrogen Energy 2012, 37, 3772-3778.*
Slaman, M. et al, SPIE 2012, 8368, paper 836805, 8 pages.*
Liu, Y. et a, Review of Scientific Instruments 2012, 83, paper 075001, 5 pages.*
Westerwaal, R. J. et al, International Journal of Hydrogen Energy 2013, 38, 4201-4212.*
Ma, G.-M. et al, IEEE Transactions on Dielectrics and Electrical Insulation 2014, 21, 380-385.*
Ngene, P. et al, Advanced Functional Materials 2014, 24, 2374-2382.*
Vijayalakshmi, K. et al, Ceramics International 2014, 40, 6171-6177.*
European Patent Office, International Search Report & Written Opinion issued in corresponding Application No. PCT/EP2016/060805, dated Aug. 4, 2016, 13 pp.
European Patent Office, Extended Search Report issued in corresponding Application No. 15167999.0, dated Oct. 28, 2015, 10 pp.
Chiadini, F. et al., "A Reflectometric Optical Fiber Temperature Sensor," IEEE Sensors Journal, Vo. 3, No. 1, Feb. 2003, pp. 80-86.
Mak, T. et al., "Optical fiber sensor for the continuous monitoring of hydrogen in oil," Sensors and Actuators B 190, 2014, pp. 982-989.
Tao, S. et al., "A fiber optic temperature sensor with an epoxy-glue membrane as a temperature indicator," Sensors and Actuators B 119, 2006, pp. 615-620.
European Patent Office, International Preliminary Report on Patentability issued in corresponding Application No. PCT/EP2016/060805, dated Sep. 6, 2017, 21 pp.

* cited by examiner

OPTICAL SENSING SYSTEM FOR DETERMINING HYDROGEN PARTIAL PRESSURE

Aspects of the present disclosure relate to an optical sensing system for hydrogen in a fluid, and to an electrical device including such a sensing system. In particular, aspects relate to an optical sensing system for sensing hydrogen in liquid-filled electrical equipment, and more particularly to oil-filled electrical transformers having such an optical sensing system for hydrogen.

TECHNICAL BACKGROUND

Insulation-liquid-filled electrical equipment, such as oil-filled shunt reactors, bushings, and especially transformers such as power and distribution transformers, are filled with insulation liquid, in particular oil, for cooling and electrical insulation purposes. Faults inside the electrical equipment as well as degradation of the insulation liquid and of other insulation components such as insulation paper provided within the electrical equipment can form decomposition gasses which mainly dissolve into the liquid. This is valid for equipment employing both mineral oil and oil from natural sources.

It is important to detect such faults, errors and degradations early, since especially transformers are important components of the electrical grid, and their failure can be very costly. Hence, a transformer is supposed to operate continuously and as error-free as possible over many years or even decades.

The quantity and composition of the decomposition gases is dependent on the underlying defect: A large fault with high energy content, such as rapid overheating or arcing, causes large amounts of gas to be produced in a short period of time, whereas the amount of gas produced by a small fault may be relatively smaller. Also, the relative concentrations of the different gasses dissolved might indicate the specific type of fault. Thus, if the nature and amount of individual gases dissolved in the insulation liquid are known, the occurrence of a change of the concentration of a specific gas in the oil can be used to identify an electrical fault in the equipment. It is known that one of the most important indicators for electrical failure in oil insulated transformers is the occurrence of hydrogen gas dissolved in the oil, which is for example produced at a faulty portion of an insulation of a winding of the transformer by thermal or electrical decomposition of the oil. For this reason, it is desirable that such errors, which may eventually cause complete failure of the transformer, can be detected as early as possible by identifying a rise in hydrogen concentration. This should ideally be possible at a stage when appropriate countermeasures may still be taken before serious and potentially costly malfunction occurs.

At a very early stage of such an electrical fault, only a very small amount of hydrogen gas may be produced, which dissolves in the oil and thus a concentration of dissolved hydrogen builds up in the oil over a longer period of time—whereby the hydrogen concentration in the oil may, at least during an early phase of the failure, even be below a threshold at which it can be detected with most known detection methods.

Most modern electrical transformers in power grids are still not equipped with on-line or real-time monitoring devices for such gasses. In order to control and evaluate the health of these transformers, an oil sample from the insulating oil bath is periodically taken and sent to qualified laboratories where the dissolved gases and other oil properties are measured. This monitoring method is time consuming, lacks continuity, has the risk of human error and is highly priced. Even if this costly method is carried out more frequently, there are several possible sources for error in the process, for example changes in the chemical and physical properties of the probe during the transport between the point in time when the probe is drawn, and the moment when the gas content is actually determined in a laboratory. Also, this method does not provide any information on where a fault occurred in the transformer. Thus, this method shall be of no further interest here, even though it is still widely used.

On the other hand, in online-methods the gas concentration in the insulation liquid is monitored directly and (quasi-)continuously. For this purpose, monitoring systems exist, sometimes built-in, for measuring hydrogen in transformer oil. These systems are based on different sensing techniques. They include, for example, semiconductor sensors, thermal-conductivity analyzers, pellistors, and fuel cell sensors, amongst others. These sensing techniques usually require a complicated gas separation system that adds complexity and cost to the sensor design and calibration. Thus, these devices are generally cumbersome and expensive. Additionally, some of these monitoring techniques suffer from cross-sensitivity towards other gases present in the oil, which additionally makes the results less reliable.

Therefore, even advanced transformers, i.e. those equipped with a dedicated on-line gas monitoring system, are often still additionally and periodically verified with expensive laboratory tests to reassure the accuracy of the on-line gas monitoring system.

There have been proposals for such on-line hydrogen monitoring devices which include thin film based fiber optical sensors, wherein a sensing material changes its optical properties upon an exposure to hydrogen dissolved in the oil. One such system for detecting hydrogen gas is described as an optical switching device in WO 2007 049965 A1. Another proposal is provided in "Optical fiber sensor for the continuous monitoring of hydrogen in oil" by T. Mak, R. J. Westerwaal, M. Slaman, H. Schreuders, A. W. van Vugt, M. Victoria, C. Boelsma, B. Dam, in: Sensors and Actuators B 190 (2014) 982-989. Thereby, the proposed optical sensors include a sensitive film comprising, for example, an alloy of Mg and Ti, capped with a Pd-containing layer. For the hydrogen detection, metal hydrides thin films can be used since they change their optical (and also electrical) properties upon exposure to hydrogen.

The kinetics as well as the thermodynamics of such thin film based hydrogen sensors is temperature dependent, and sensors based on this concept require information of the temperature of the sensor in order to correctly determine the hydrogen concentration. The solution to this is typically to provide a standard temperature sensor added to the sensing device. However, temperature sensors are additional devices which increase the complexity and costs of a product, and moreover they are sensitive to magnetic fields which are generally present inside transformers, thereby potentially causing an erroneous hydrogen reading. Therefore, in case of the presence of magnetic fields such as in transformers, solutions are preferred where a part of the thin film structure of the fiber optical sensor itself is used for the temperature determination. The state-of-the art solution to this is addition of a further thin layer, which is used to determine the temperature using physical principles as, for instance, interference and expansion/contraction of the sensor itself. Such a sensor is described in the article "A fiber optic temperature sensor with an epoxy-glue membrane as a temperature indicator", S. Tao, A. Jayaprakash, Sensors and Actuators B 119 (2006) 615-620. It refers to a fiber optic temperature sensor for the monitoring/detecting of the ambient temperature. This sensor is based on polycyclic aromatic compounds (PAHs) as the temperature indicator, which fluoresce when excited with UV light, wherein the intensity of the fluorescent light is dependent on the temperature. This temperature-dependent behavior of the added fluorescent layer is then used to determine the temperature, which may then be employed in determining the hydrogen concentration from the signal of actual thin film optical hydrogen sensor.

A related principle is described in "A reflective fiber optic temperature sensor using silicon thin film", J. w. Berthold, S. E. Reed, R. G. Sarkis, Optical Engineering 30(5), 524-528 (1991). The method is based on the change, with temperature, of the intensity of light being reflected from a thin silicon film which is deposited on the end of an optical fiber.

Further, "A Reflectometric Optical Fiber Temperature Sensor", F. Chiadini, A. Paolillo, and A. Scaglione, IEEE Sensors Journal, vol. 3, no. 1, (2003), describes a reflectometric fiber-optic temperature sensor which is based on replacing the fiber cladding with a temperature sensitive liquid on a short length of the fiber.

In the above described concepts, the extra layer or coating required for temperature determination, additional to the hydrogen-sensitive layer itself, adds cost in the production, requires additional apparatus features for the temperature determination, and thus adds cost in the form of construction and production effort. Moreover, the complexity of the optical sensing system for hydrogen is generally enhanced, and so is probability for failure.

US 2014/374578 A1 discloses a device for the detection and/or quantitative analysis of hydrogen, intended for monitoring an installation. The device comprises a first measuring optical fiber intended to equip the installation, and an optical system optically connected to the first measuring optical fiber.

US 2015/063418 A1 discloses an apparatus for estimating a parameter, which includes an optical fiber sensor configured to be disposed in a downhole location and including at least one sensing location configured to generate measurement signals. A light source is configured to transmit a measurement signal having a wavelength to interrogate a sensing location and cause the sensing location to return a reflected measurement signal indicative of a measured parameter.

US 2009/210168 A1 discloses a signal processing apparatus which has an input for receiving a signal conveying a response from first and second optical components, which are in an optical sensor, to an optical excitation. A signal processing apparatus has a processing entity for processing the response from the first and second optical components to derive information on a hydrogen concentration in the optical sensor.

In view of the above and for other factors, there is a need for the present invention.

SUMMARY OF THE INVENTION

In view of the above, an optical sensing system, a method for sensing hydrogen in a fluid, and a device for electric power generation, transmission, or distribution are provided.

According to a first aspect, an optical sensing system for sensing hydrogen in a fluid is provided. It is adapted for employing measurement values of at least two differing optical sensors and comprises a first optical sensor comprising a first optical fiber, wherein an end portion of the first optical fiber is coated with a first hydrogen-sensitive multilayer on an end surface perpendicular to a longitudinal axis of the first optical fiber, the first multilayer being adapted to change its optical properties, in particular its optical reflectance, dependent on a hydrogen partial pressure in the fluid and dependent on a temperature of the fluid, with a known first characteristic; a second optical sensor comprising a second optical fiber, wherein an end portion of the second optical fiber is coated with a second hydrogen-sensitive multilayer on an end surface perpendicular to the longitudinal axis of the second optical fiber, the second multilayer being adapted to change its optical properties, in particular its optical reflectance, dependent on the hydrogen partial pressure in the fluid and dependent on a temperature of the fluid, with a known second characteristic which is different from the first characteristic; at least one light source adapted for coupling light into the first optical fiber and the second optical fiber, at least one light detector adapted for detecting light reflected by the first multilayer and light reflected by the second multilayer, a control unit operably coupled to the at least one light detector, adapted for calculating the hydrogen partial pressure in the fluid, by using the first characteristic and the second characteristic and an output signal of the at least one light detector.

According to second aspect, a method for sensing hydrogen in a fluid is provided. The method comprises providing an optical sensing system according to a first aspect, providing the first optical sensor and the second optical sensor in the fluid in which the hydrogen shall be sensed, coupling light from at least one light source into the first optical sensor and the second optical sensor, detecting light reflected from the first optical sensor and the second optical sensor, and determining, from the intensity of the reflected light from the first optical sensor and the second optical sensor the hydrogen partial pressure in the fluid.

According to a further aspect, a device for electric power generation, transmission, or distribution comprises an oil volume, and an optical sensing system according to the first aspect.

Further advantages, features, aspects and details that can be combined with embodiments described herein are evident from the dependent claims, the description and the drawings.

Embodiments have the advantage over known solutions, in that conventional thin film based hydrogen sensors require external temperature information from an additional device or extra sensing layer, while in embodiments the temperature is derived as an intrinsic property of the actual thin film structure. Thus, a conventionally required dedicated temperature-measuring device is omitted, which makes the system less complicated, more stable and less costly. An additional benefit is that, since the sensing stacks are fully optical, their responses do not depend upon external perturbations such as strong magnetic fields as present in a transformer, much unlike conventional temperature sensors. Different as in a certain art, there is also no need for an additional layer within the optical sensor, which might influence the hydrogen sensitivity, precision, and/or lifetime of the sensor. The fact of having two or more sensing stacks—or multilayers—further has the benefits of an increased hydrogen sensitivity of the hydrogen sensing system, since both stacks operate in the same range, although with different characteristics. Another advantage is that it consequently makes the hydrogen sensing device redundant.

BRIEF DESCRIPTION OF THE FIGURES

More details will be described in the following with reference to the figures, wherein.

DETAILED DESCRIPTION OF ASPECTS OF THE INVENTION

Figure 1:
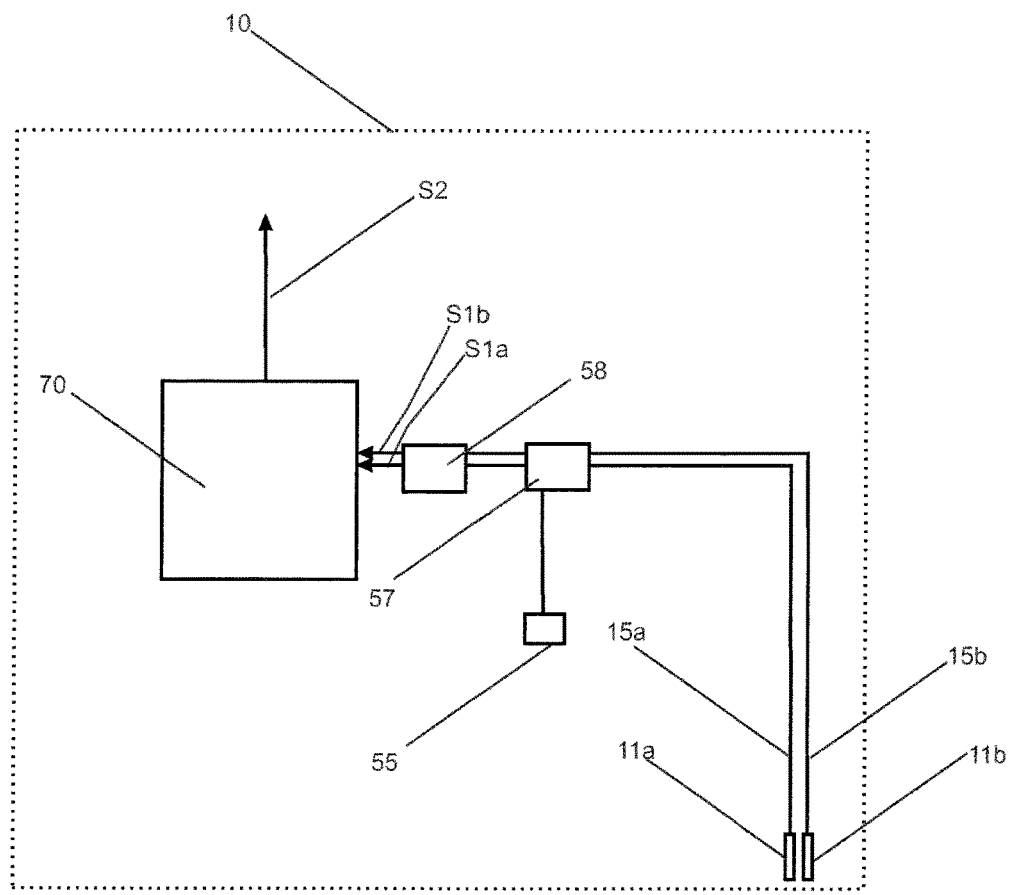
FIG. 1 is a schematic view of an optical sensing system according to embodiments.

As used herein, metal alloys defined by a formula with atomic percentage values typically adding to 100 percent, such as, for example, $Mg_{52}Ni_{20}Zr_{28}$, are meant to also include substances with a composition deviating from that with the exact numbers provided. Typically, alloys having a composition wherein each number, independently from each other, has a tolerance of +/−15 percent, are still regarded to fall under the metal alloy provided by provision of the exact formula, such as the example above, also if the single numbers do not add up to 100 in total. Also, as used herein, such alloys may comprise further, non-named substances such as chemical elements of smaller amounts, such as up to about 2 percent each, but not more than about 10 percent in total.

As used herein, the term "fluid" is intended to be both representative for gases and liquids. It is, however, mainly used to be representative of an insulation liquid, particularly an oil, which is part of the insulation and/or cooling system of an electrical device, more particularly of a power transformer.

It is noted that as used herein, the term "optical sensor" comprises mainly an optical fiber which is coated with a multilayer having a sensing layer which is hydrogen-sensitive. However, this is purely a matter of pragmatical definition/convention; it might as well have been defined that the optical sensor comprises only the multilayer, and that the optical fiber is an item external to the optical sensor. Thus, the term "optical sensor" should not be interpreted in a narrow sense, such as literally described herein. The optical sensor might also be a transparent (e.g. glass, plastic) substrate coated with a hydrogen-sensitive multilayer as described, for example.

In the following, some aspects of the invention are described in detail. Aspects and parts of aspects are independent of each other and can be combined in any manner. For example, any aspect or embodiment described in this document can be combined with any other aspect or embodiment, as long as the combinations achieved are technically feasible.

Aspects of the invention disclose a method and apparatus for determining the hydrogen concentration using thin film sensors, while employing two or more optical sensors, which typically, but not necessarily, have the same working principle and basic physical structure. Thereby, a conventional dedicated temperature probe is omitted. The optical sensing system according to aspects can, for example, be used in the determination of dissolved hydrogen in transformer oil using fiber optical sensors. Aspects relate to a combination of two selected and calibrated hydrogen sensing stacks provided on a transparent carrier body, which may be for example a glass substrate, or typically an optical fiber. Besides both determining the hydrogen concentration, the two or more optical sensors together enable deduction of the true sensor temperature (hence the temperature of the surrounding fluid) when both sensors are on the same temperature level—what is typically the case, especially when they are located adjacent to each other or even located close to one another. Moreover, the presence of two sensors instead of one, as in conventional techniques, increases the hydrogen sensitivity in selected ranges and makes the system redundant. Given the relatively low price of optical fiber based hydrogen sensors, the second, additional sensor does hardly influence the final costs of such an optical sensing system for transformer monitoring. In most aspects described herein, the optical sensors are optical fiber sensors, wherein one end portion of each fiber is coated with a layer stack (herein also called multilayer), which changes its optical properties such as reflectance and transmission when exposed to a hydrogen partial pressure.

In aspects, it is also possible to use other types of sensors such as, for example, a glass substrate which has two zones with different applied coatings/multilayers, and wherein each zone with its coating is used as an individual optical sensor, such as if the coatings were provided on two different optical fibers. Hence, each zone is illuminated with a light source, or both with a common light source, and the reflected or transmitted light from each zone is measured by a light detector, or by one dedicated light detector each, such as a photo diode.

In aspects, the temperature of the sensors, that is typically the one of the surrounding medium, is deduced from the difference of the optical responses of two hydrogen sensing layers, or layer stacks, in the optical sensors. Thus, there is no need for an external temperature sensor. Thereby, the optical sensing system according to aspects may be advantageously employed in a number of aspects, which may also be combined. On the one hand, the optical sensing system may be used to measure the hydrogen partial pressure, or hydrogen concentration, in a fluid surrounding the optical sensors. Thereby, the temperature may not even be explicitly calculated as an output value of the system, but be intrinsically used in the control unit of the sensing system. Secondly, both effects may be combined, that is, the hydrogen partial pressure and the temperature are both provided as output values by the sensing system. Thirdly, the optical sensing system may be employed as a temperature measuring device only, for fluid atmospheres containing a hydrogen partial pressure, for example in chemical process vessels, tanks, and the like.

In aspects, the optical sensing system is adapted for sensing a status condition of an insulation-liquid-filled electrical equipment. Herein, electrical equipment refers to any equipment such as shunt reactors, bushings and transformers. The invention is particularly suited for the insulation liquid being insulation oil, be it on a mineral basis or from organic sources, such as palm oil. The invention is further particularly suited for the electrical equipment being a transformer, such as a power or distribution transformer, and more particularly for an oil-filled transformer.

The status condition of the electrical equipment is herein expressed by the hydrogen content (or hydrogen concentration) of the insulation liquid, which is a reliable indicator of various conditions, in particular fault conditions. The hydrogen content is defined as the amount of hydrogen dissolved in the insulation liquid (in ppm). A hydrogen sensitive layer (henceforth also called sensing layer) of each of the optical sensors is arranged in communication with the fluid (insulation liquid, oil), and is preferably immersed in the insulation liquid, so that the amount of hydrogen dissolved in the insulation liquid results in a characteristic partial pressure of hydrogen at the optical sensors, this partial pressure being a function of the hydrogen content (in ppm) in the insulation liquid. This relation depends on additional parameters such as the temperature of the insulation liquid and/or of the hydrogen sensitive layer, and on the type of oil used in the transformer. Herein, the term "hydrogen" may refer to hydrogen molecules or atoms (which may be radicals). As used herein, the sensing layer "being in communication with a fluid" means that the gaseous components of interest present in the fluid, in particular hydrogen, may reach the sensing layer, even if other layers for catalysis, protection or the like are located between the sensing layer and the fluid. The metal alloy of the sensing layers of the stacks of the optical sensors reacts with this hydrogen from the fluid, which diffuses through a protection layer, and builds a metal-alloy hydride system. The latter reaction is a reason for the change in optical properties of the sensing layers when hydrogen is present, which is used for a hydrogen detection in aspects as described above.

Next, some aspects relating to the light source arc described in more detail. Herein, light is defined as electromagnetic radiation. The radiation may have any wavelength, but is preferably in one of the mid-1R, near-1R, and visible wavelength ranges.

Next, some aspects relating to the two or more optical sensors for sensing hydrogen are described in more detail. The optical sensors for detecting hydrogen are optically coupled to a light source for receiving light from the light source. The optical sensors each have a sensing layer that changes its optical response with respect to the received light, in particular its reflectance (or if measured by the sensor: transmittance), depending on an amount of hydrogen present in the sensing layers. This means, a changing hydrogen partial pressure also leads to a change in reflectance of the sensing layers. As the sensing layers are part of the optical sensors, the optical sensor also changes its reflectance.

The two or more optical sensors of the optical sensing system are configured such that the sensing layers are immersed, during operation, in the insulation liquid of the electrical equipment. The measured optical response of the optical sensors may include transmission, reflection, absorption and/or other properties detectable by typical light detection devices, such as photo diodes.

According to an aspect, the optical response is a reflection, and the at least two optical sensors (more precisely, their sensing layers) are mounted (e.g. laminated or coated) to an end portion of a light guiding substrates coupling the optical sensors to the light source and to the light detection device(s) (possibly via other optical conducting materials as well). In particular, the light guiding substrate is an optical fiber, wherein the sensing layer is coated to an end surface of a core of the optical fiber. Typically, the sensing layer is part of a multilayer structure, which also comprises a catalyst layer which includes Palladium (Pd). Further, auxiliary layers comprising Titanium (Ti) may be provided between the core of the optical fibers and the sensing layer, and between the sensing layer and the catalyst layer. Also, typically the outermost layer of the multilayer is a coating layer, which protects/shields the sensing layer and the catalyst layer from the insulation liquid, which is typically present in the form of an oil volume.

In aspects, the sensing layers for hydrogen comprise a metal alloy that changes its optical response depending on the amount of hydrogen present in the fluid surrounding the optical sensors and thus also the sensing layers/sensing stacks, which is in aspects the insulation liquid, in particular oil used for insulation of an electrical device.

The optical sensors according to aspects, which typically include a thin film of a metal alloy as a sensing layer each, may comprise a multimode optical fiber in combination with a fiber-tip micro-mirror configuration including that sensing layer. The micro mirror comprises the multilayer described earlier. In order to sense the hydrogen concentration in the fluid in a continuous way, a single hydride forming metal as a sensing layer, like for example Pd or Mg, is typically not suited, due to the metal-hydride phase transition at a single plateau pressure and temperature, or due to limited "temperature-reflectance-isobar" characteristics. Therefore, one needs to alloy the metal thin films with suited other metal(s) to obtain a temperature-reflectance isobar with non-negligible slope in the desired pressure and temperature range. For example, by doping a Mg—Ni based alloy with a relatively large atom like Zr, Ta or Hf, the alloy becomes mainly amorphous, or at least shows the characteristics of an amorphous alloy: A group of these alloys according to aspects show a well-defined relation between their optical response (e.g., reflectance) and the applied hydrogen partial pressure due to their amorphousness. It was found that for some particular alloys, the temperature-reflectance isobar has particularly useful characteristics in the hydrogen concentration and temperature range which is of interest for measuring hydrogen partial pressures in the insulation liquids of electrical equipment, in particular power transformers. It was found that with a Mg—Ni-M based alloy as a hydrogen sensing layer, wherein M is Zr, Ta, or Hf, it is possible to continuously monitor the hydrogen concentration in the oil of an operating power transformer, and thus to check for the condition of that power transformer. Thereby, the optical sensors typically comprise sensing layers with a different chemical composition, that is, in the previous example of Mg—Ni-M, the relative proportions between the single elements in the alloy may vary between the sensing layers of the optical sensors. Alternatively, the component M may be a different element in both optical sensors. Also, the composition of the sensing layers may be identical, but the physical properties of both sensing layers may be manipulated during manufacturing, for example by influencing the degree of amorphousness.

In aspects, the Mg based complex metal hydrides may be covered with protective coatings including PMMA, PTFE, $SiO_2$, and Aluminum Oxide, in particular $Al_2O_3$.

In aspects, further examples for Mg alloys which may be used for the sensing layers are Mg compounds such as Mg—Ni compounds and Mg—Ti compounds, or Mg, V, Y or other compounds thereof Particularly, Mg—Ni compounds showing this effect are $Mg_2Ni$. For example, $Mg_2Ni$ has a relatively high reflectivity, but under the influence of surrounding hydrogen at least a portion thereof is converted to $Mg_2NiH_4$, which is much less reflective at room temperature.

According to aspects, the control unit comprises an input section for receiving at least one signal from the at least one light detection device, which detects the light from the light source(s) after being reflected in the optical sensors. If there is only one light sensor, the signal carries the information of both sensors, then it should be ensured that the signals from the two sensors are distinguishable by the control unit. This may for example be provided by achieving a time multiplexed reflectance signal by having two independent and intermittently shining light sources, one for each sensor. Thus, each sensor may have a single dedicated light source, or both may be fed by the same source, but then two distinct sensors are necessary. The same goes for the light detector. A signal analyser in the control unit serves for analysing the output signal of the light detection device(s). The light detection device may for example be a photo diode, a spectrum analyser, or other principally known devices suitable for analyzing the reflected light from the optical sensor. The control unit has stored an individual parameter matrix of isobars of temperature and optical contrast (e.g. reflectance) for each of the sensors. The matrix of each sensor typically covers the respective values in a temperature range of interest from 10° C. to 100° C., and for a hydrogen partial pressure range from 10 ppm to 1000 ppm. The control unit then looks up the actual readings from the optical sensors and determines, from each parameter matrix, to which hydrogen partial pressure and temperature there is a fit in both matrices. Thus, the actual temperature of the fluid and the partial pressure are determined. It shall be noted that the choice of the type of graph showing the relation between pressure p, temperature T, and optical reflectance R is arbitrary. It may be chosen as a pressure-reflectance-diagram, or as a temperature-reflectance-diagram. Depending on the type of diagram, isotherms may show as straight lines (T-R-diagram) or as curves (p-R-diagram).

The control unit may comprise a visual output element, which is configured for displaying a signal depending on the detected hydrogen level. For example, the hydrogen level may be output on a numerical display having seven-segment displays, or on a monitor such as an LCD monitor. Also, the control unit may be configured to calculate a timely deviation of the hydrogen signal, and to display an alert, for example as a red light, when the deviation is positive or exceeding a boundary value, indicating a rise in hydrogen concentration, which is regarded as being caused by a fault in the electrical device such as the transformer which is monitored.

According to aspects, an electrical equipment with an insulation liquid is provided, wherein the optical sensor described herein is immersed in the insulation liquid (i.e. partially immersed so that the optical sensor is at least in partial contact with the insulation liquid).

Detailed Description of the Figures and Embodiments

In FIG. 1, an optical sensing system 10 for hydrogen in a fluid according to embodiments is shown. The optical sensing system 10 is adapted to use or employ measurement values of at least two optical sensors 11a, 11b, which are hydrogen-sensitive and typically immersed in the fluid (which is not shown in FIG. 1, see e.g. FIG. 6). A first optical sensor 11a comprises a first optical fiber 15a, wherein an end portion 18a of the first optical fiber 15a is coated with a first hydrogen-sensitive multilayer 20a adapted to change its optical properties dependent on a hydrogen partial pressure in the fluid 12. A second optical sensor 11b comprises a second optical fiber 15b, wherein an end portion 18b of the second optical fiber 15b is coated with a second multilayer 20b, also adapted to change its optical properties dependent on a hydrogen partial pressure in the fluid 12. The light from a light source 55 is coupled via a coupler 57 and the first and the second optical fibers 15a, 15b into the optical sensors 11a, 11b. The hydrogen-sensitive multilayers 20a, 20b (not shown in FIG. 1, see FIG. 5) of the optical sensors 11a, 11b are provided such that they have a different sensing characteristic for hydrogen, that is, for the same hydrogen partial pressure at both optical sensors 11a, 11b at the same temperature, the optical sensors 11a, 11b have a different reflectance and transmittance with respect to each other— which is fulfilled for the measurement range of interest, i.e. at least 10 ppm to 1000 ppm hydrogen partial pressure in the fluid, and 10° C. to 100° C. fluid temperature. The respective characteristic is known for both optical sensors 11a, 11b and is stored as an individual parameter matrix for each of the sensors 11a, 11b in a memory of the control unit 70. The characteristics are either predefined during construction/ production of the optical sensors 11a, 11b, and/or the optical sensors may be characterized for the whole measurement range of interest prior to their application in the field, that is, typically at the factory or production site.

The reflected light from both optical sensors 11a, 11b is detected by at least one light detector 58, which provides two different—typically electrical—signals S1a and S1b, indicative of the reflected light from one of the optical sensors 11a, 11b each. The control unit 70 uses these signals, together with optical sensor specific parameter matrices described further below, to determine or calculate an output signal S2. S2 may comprise values for the temperature of the fluid 12, for the hydrogen concentration/partial pressure in the fluid 12, or both. Hence, S2 may be a scalar or a vector, depending on the individual design, purpose and usage of the optical sensing system 10.

Figure 2:
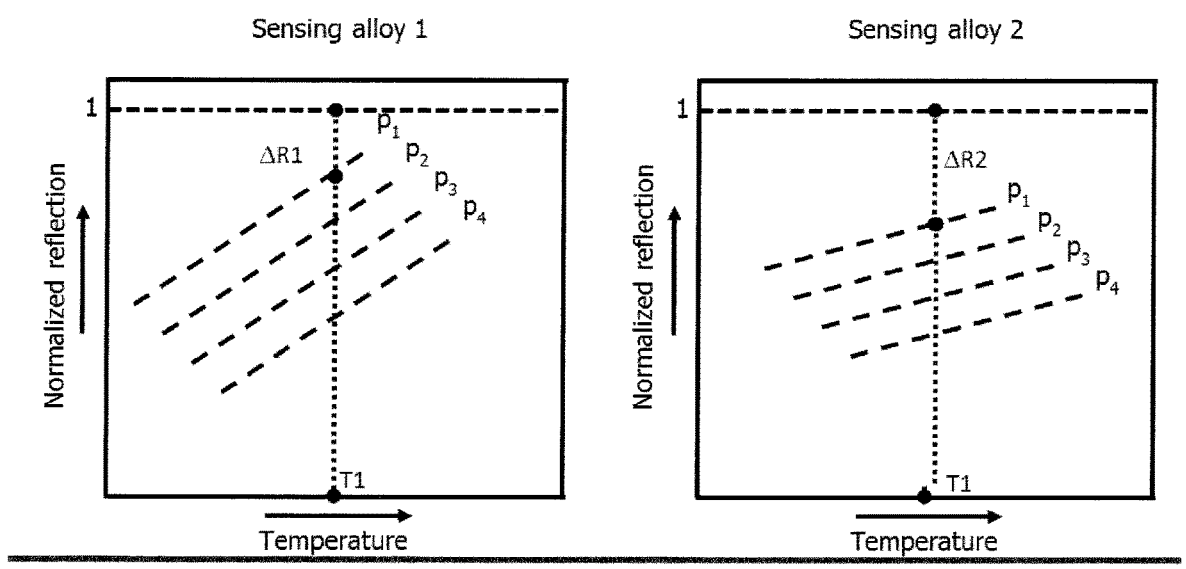
FIG. 2 is an illustrational schematic view of the sensing characteristics of two different, hypothetical sensing layers of two optical sensors from an optical sensing system according to embodiments.

The difference in the characteristics between each of the optical sensors 11a, 11b is predominantly defined by the difference between the respective sensing layers 24a, 24b of the multilayers 20a, 20b. The characteristics may be individually expressed by a set of isobars of temperature and optical reflectance, such as exemplarily shown in FIG. 2. Thereby, for illustrational purposes, the temperature is shown on the x-axis, the normalized reflection of the respective sensing layer is shown on the y-axis, and lines for a constant hydrogen partial pressure (isobars) are indicated as dashed lines. The left graph shows an example of four, just exemplarily chosen, isobars of a first sensing alloy 1 of a first sensing layer 24a of a hypothetical first optical sensor 11a, while the right graph shows the same for a second sensing alloy 2 of a second sensing layer 24b of a hypothetical second optical sensor 11b with a different characteristic. In embodiments, the first sensing alloy 1 (left) may form the first sensing layer 24a of a multilayer 20a of the first optical sensor 11a, and the second alloy may form the second sensing layer 24b of the second multilayer 20b of the second optical sensor 11b. For a measured change in reflection ΔR1 for the first sensing layer (left) and ΔR2 for the second sensing layer (right), one can then obtain the unique temperature and thus the hydrogen concentration in the fluid, such as transformer oil. To this end, the two parameter matrices behind the diagrams are employed, which can also be regarded as hydrogen pressure-temperature-optical reflectivity parameter landscapes for each of the first optical sensor 11a and second optical sensor 11b. Thereby, the determination of the fluid temperature and/or hydrogen partial pressure (or concentration) with an optical sensing system 10 according to embodiments is based on the following principle. In order to be able to determine the temperature with sufficient precision, or in an accurate way, a different hydrogen pressure level should result in a well separated measurable change in reflection between both optical sensors 11a, 11b. The resolution of this system is, amongst other factors, determined by the distance between the different pressure-reflection-isobars, see FIG. 2, in conjunction with the measurement precision of the optical sensing system 10. It goes without saying that with a higher resolution and precision of the control unit and the at least one light detector 58, a smaller difference in optical response between the first optical sensor 11a and the second optical sensor 11b may be compensated. On the other hand, the accuracy of the temperature and hydrogen partial pressure measurement is increased, provided that the rest of the system is left unchanged, when the difference in the characteristics between both optical sensors 11a, 11b becomes—generally speaking—larger. It is understood that for different preferred temperature ranges and hydrogen partial pressure ranges of interest, suitable materials, or more precisely pairs of materials, for the two sensing layers 24a, 24b may be readily found by means of experimentation. Thereby, in order to obtain unique temperature and hydrogen partial pressure results over the whole ranges of interest for both of the parameters, the graphs such as shown in FIG. 2 should rather not exhibit regions where the characteristic curves have a plateau, meaning that the isobars in FIG. 2 should not have horizontal parts. In the theoretical case of a plateau, it is clear that for a certain measured change in reflection $\Delta R1$ or $\Delta R2$ for the respective optical sensor 11a and 11b, there may exist at least two or more possible temperature values. This might render the unique determination of the temperature difficult or even impossible. However, plateau regions in a sensor characteristic may also be acceptable, for example when they are located outside the temperature and hydrogen partial pressure ranges of interest in the particular application or purpose.

Figure 3:
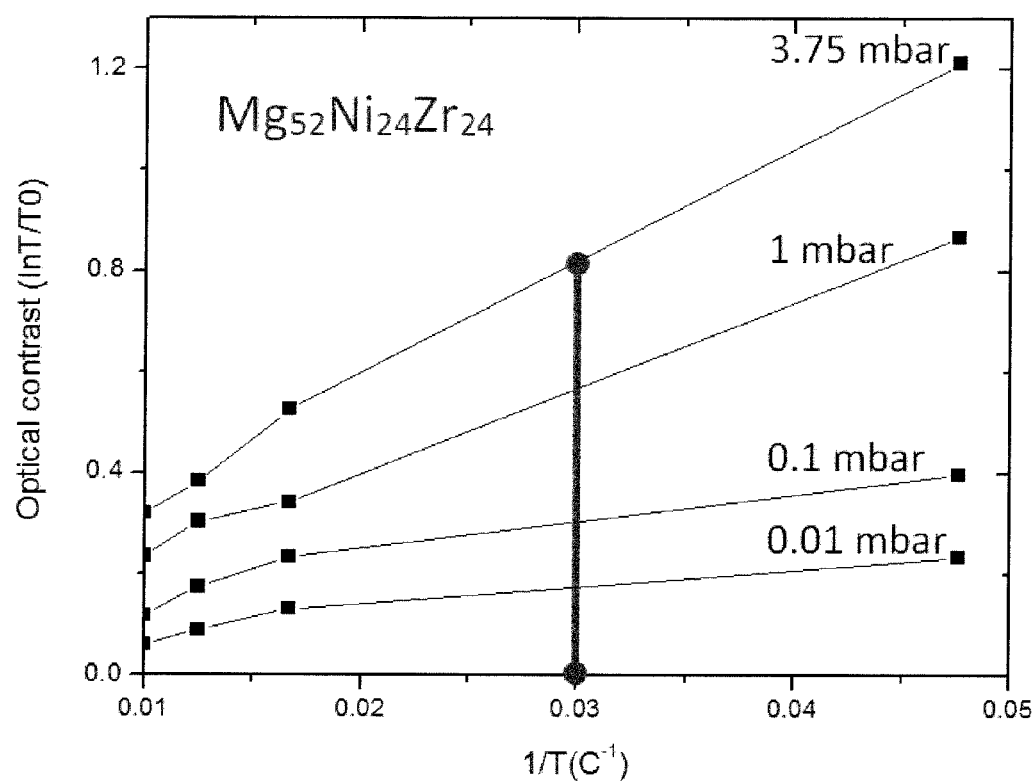
FIG. 3 shows an experimental graph of a sensing layer material, similar to FIG. 2.
Figure 4:
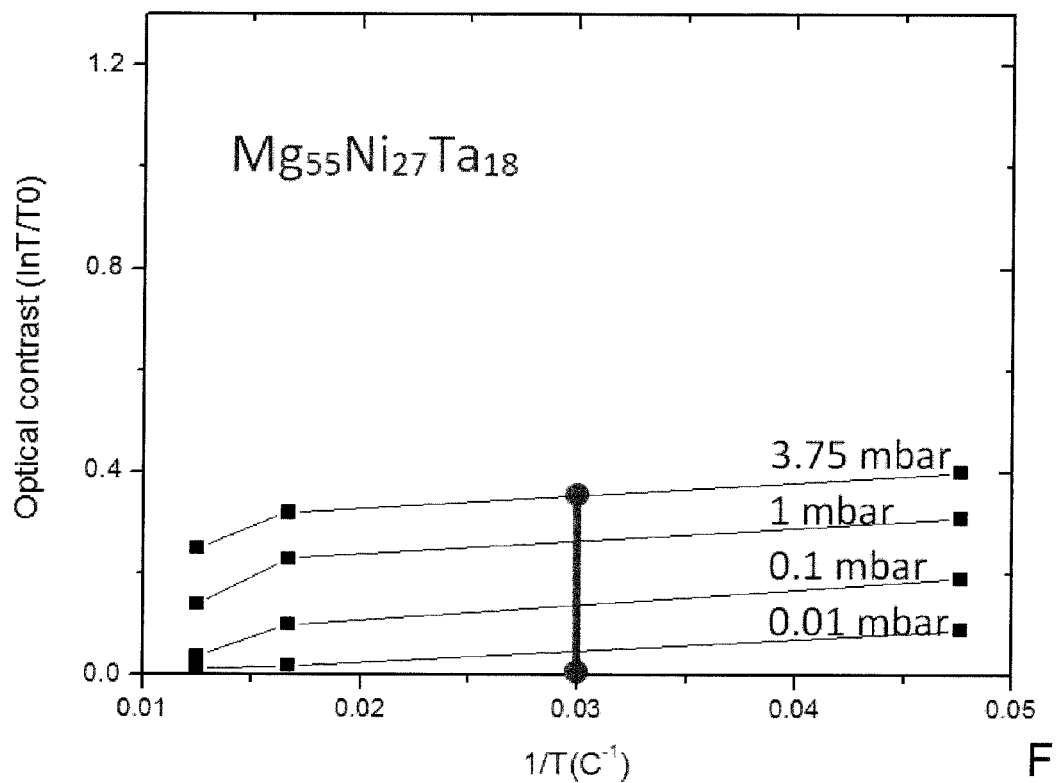
FIG. 4 shows an experimental graph of a sensing layer material, similar to FIG. 3.

Experimental support of the graphs in FIG. 2 is given in FIGS. 3 and 4, where the experimentally determined pressure-temperature-reflection parameter landscape of two appropriate sensing layers 24a, 24b of two multilayers 20a, 20b of two optical sensors 11a, 11b are shown. The materials are, as non-limiting examples for demonstration only, $Mg_{52}Ni_{20}Zr_{24}$ (FIG. 3) and $Mg_{55}Ni_{27}Ta_{18}$ (FIG. 4).

FIG. 3 shows the experimental temperature dependence of the optical response in transmission (ln T/T0) at different hydrogen pressures for a $Mg_{52}Ni_{24}Zr_{24}$/Pd thin film. FIG. 4 shows the experimental temperature dependence of the optical response in transmission (ln T/T0) at different hydrogen pressures for a $Mg_{55}Ni_{27}Ta_{18}$/Pd thin film. These figures show that the temperature can be determined uniquely, once the pressure-temperature-optical response landscapes are known, from the readings of the at least two optical sensors employing the at least two different sensing layer materials. Thus, the output signals in reflection (which is directly inversely related to the transmission shown in FIG. 3 and FIG. 4) from the optical sensors are employed in the control unit 70 (see FIG. 1) to look up, for each optical sensor 11a, 11b individually, which temperature and hydrogen partial pressure is fitting the measured reflection value. This may for example be carried out by employing a least-square-algorithm or the like. By so correlating the values for both optical sensors 11a, 11b, typically one unique value for temperature and one for hydrogen partial pressure is calculated, respectively obtained. Either of these two parameter values may be used for display or be transmitted as an output value to an external computer system, for example. Hence, with an optical sensing system with at least two optical sensors 11a, 11b, both the temperature and the hydrogen partial pressure in a fluid 12 surrounding the optical sensors 11a, 11b may be obtained simultaneously, without the need for a dedicated temperature probe and/or the need for an extra dedicated temperature sensitive layer in the optical sensors 11a, 11b.

The optical sensing system 10 comprises sensing layers including thin metal films with a typical thickness from 5 to 500 nm, more typically from 15 nm to 300 nm. These may in embodiments be deposited using, e.g., an ultrahigh-vacuum (UHV) DC/RF magnetron sputtering system, laser ablation or simple evaporation on for example glass substrates. The sticking of the thin metal film on the substrate, typically the end of the optical fiber, can be improved by using a thin interlayer of, for example, titanium. A Pd (alloy) cap layer can be used to protect the hydrogen sensing layer from oxidation and to catalyse hydrogen dissociation. An additional Ti layer can be considered between the catalytic Pd layer and the hydrogen sensing layer, to prevent undesired alloying effects between these two. This multilayer is protected by an additional coating on top of the Pd-based layer to protect the optical sensors 11a, 11b from possible contaminations in the fluid/oil and to keep the fluid/oil away from the catalytic surface.

As an experimental example, two optical fibers for the temperature determination were used, with two different alloys as the sensing layers. These are $Mg_{52}Ni_{24}Zr_{24}$ and $Mg_{55}Ni_{27}Ta_{18}$. In a characterization, firstly the optical contrast is plotted, in this case the logarithm of the normalized transmission ln (T/T0), versus the inverse of the temperature. This results in obtaining almost linear curves. In an example with these optical fiber sensors, an optical change (ln(T/T0)) of 0.82 for the $Mg_{52}Ni_{24}Zr_{24}$ sensor, and an optical change of 0.36 for the $Mg_{55}Ni_{27}Ta_{18}$ based sensor is detected. From the parameter matrices, there is only one unique combination of temperature and pressure which satisfies these values of the optical change. This point is determined to be 33° C. and 3,7 mbar. This procedure is valid and applicable even when the temperature-optical response-isobars of the two optical sensors should cross each other.

It goes without saying that the described principle can be realized in a variety of ways, with the only condition that the two or more employed sensors have a different sensing characteristic with respect to a hydrogen partial pressure. Thereby, the difference of the optical properties between the optical sensors includes that the slopes of the isobars in temperature-optical reflectance diagram should be different by a predefined percentage. How large this difference has to be is obviously strongly dependent on a number of parameters, for example the sensitivity of the light detection mechanism and its resolution. Furthermore, this should be fulfilled over at least the largest part of the temperature range of interest and the hydrogen partial pressure range of interest, so that the difference enables the control unit to determine a hydrogen partial pressure in the fluid and/or the temperature of the fluid by employing looked-up values, for each sensing layer individually, from the individual parameter matrices of isobars for the conjunction between hydrogen partial pressure, temperature and optical contrast. Thereby, the individual parameter matrices of isobars of temperature and optical contrast of the first optical sensor and the second optical sensor are typically stored in a memory of the control unit 70.

The above named difference in the sensing characteristics may be achieved by one of the following alternatives: Firstly, both sensing layers comprise materials having a different chemical composition with respect to each other. Secondly, the sensing layers comprise materials having basically the same chemical composition, but expose different optical properties when they are exposed to the same hydrogen partial pressure and temperature, due to their physical structure, which may in particular be their internal crystal structure and/or the degree of amorphousness, which may vary between both sensors intentionally caused during the deposition of the layers. Also, different types of optical sensors can be employed depending on the technical application of the sensing system; for example, a first optical sensor may be a fiber optical sensor as described above, and the second optical sensor may be, for example, a glass substrate on which the sensing layer (and protection layer, catalytic layer etc.) is provided. It is understood that various pairs of sensing materials may be found experimentally, depending on the desired measurement range, for example.

Hence, it is understood that a wide variety of materials may be employed for the sensing layers, with the precondition that the characteristics of the sensors enable a unique determination of the temperature in the hydrogen partial pressure and temperature ranges of interest. For example, if the optical sensing system shall be employed for only a narrow range of hydrogen partial pressures, e,g, from 50 ppm to 200 ppm, then a greater number of sensing layer materials will be employable, because a greater choice of sensing layer materials fulfill the precondition that they have different characteristics in the desired range.

Typically, the optical sensors have a sensing layer comprising a metal alloy. In embodiments, at least one of the materials is thereby a metal alloy comprising Mg, Ni, and M, wherein M is at least one of Zr, Ta, and Hf, and wherein the alloy has the composition $Mg_xNi_yM_z$. x is typically from 40 to 60, y is typically from 10 to 40, and z is typically from 10 to 40. For example, the metal alloys may be chosen, each one differently, from $Mg_{52}Ni_{20}Zr_{28}$, $Mg_{52}Ni_{24}Zr_{24}$, and $Mg_{55}Ni_{27}Ta_{18}$.

Thereby, the hydrogen-sensitive multilayers of the optical sensors each comprise a sensing layer 24a, 24b as described above, a catalyst layer 26a, 26b and a coating layer 28a, 28b, wherein the sensing layer may optionally also be identical to the catalyst layer. The coating layer can comprise PMMA and/or PTFE, and/or $SiO_2$ and/or Aluminum Oxide, or may have a multilayer structure comprising at least two of the former, mainly depending on the type of fluid in which the optical sensors 11a, 11b shall be applied.

The method for sensing hydrogen in a fluid, according to the described embodiments, typically comprises: providing an optical sensing system as described hereinbefore, providing the first optical sensor and the second optical sensor in the fluid in which the hydrogen shall be sensed, coupling light from at least one light source into the first optical sensor and the second optical sensor, detecting light reflected from the first optical sensor and the second optical sensor, and determining, from the intensity of the reflected light from the first optical sensor and the second optical sensor, at least one of: the temperature of the fluid, and the hydrogen partial pressure in the fluid. Thereby, as intensively described above, the difference between the at least two optical sensors, in the form of stored parameter matrices of isobars of temperature and optical reflectance, is employed in the determination by looking up the individual reflection or transmission values of the individual sensors in their respective parameter matrix.

Figure 5:
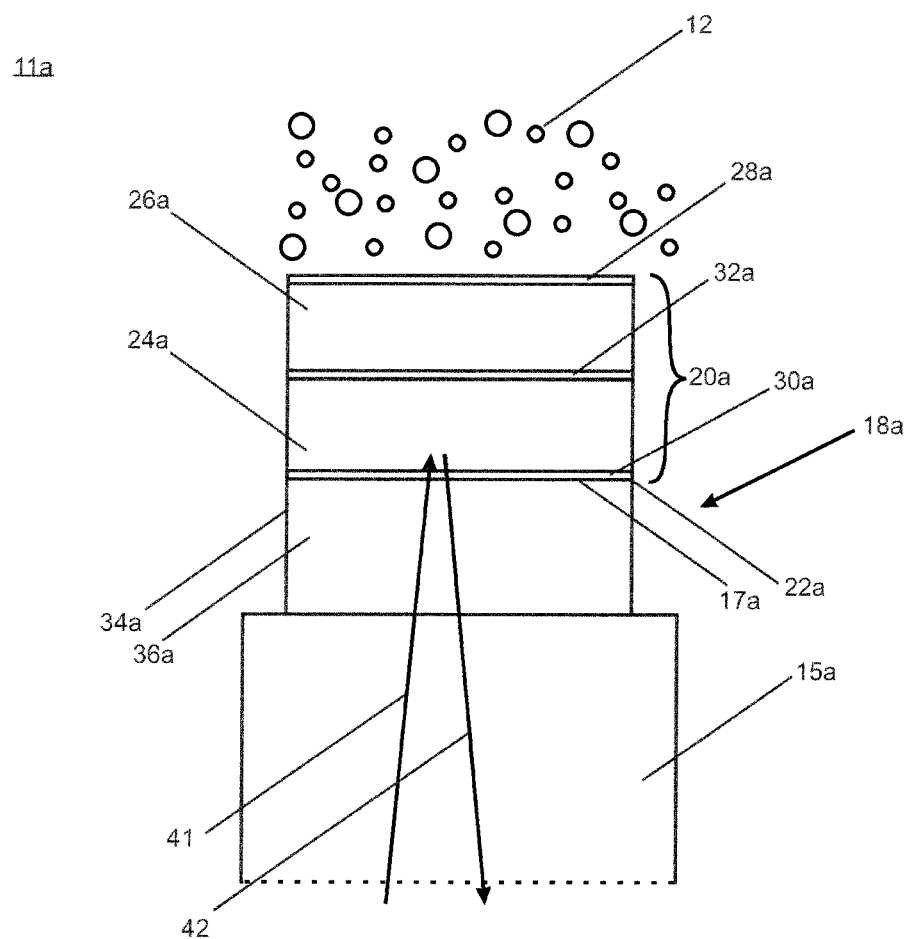
FIG. 5 is a schematic view of an optical sensor from embodiments.

In FIG. 5, a single exemplary optical sensor 11a from the at least two optical sensors 11a, 11b of an optical sensing system 10 according to embodiments is shown (see FIG. 1 or FIG. 6), comprising a multilayer 20a as described above, with a sensing layer 24a and a catalyst layer 26a. The first optical sensor 11a is, such as the second optical sensor 11b, suitable for detecting hydrogen in a fluid 12 (schematically shown, with smaller circles representing dissolved hydrogen in the fluid) which is in physical contact with the optical sensor 11a. The multilayer is coated to an end portion 18a of an optical fiber 15a. The latter typically has an outer diameter, including cladding and coating, of about 230 µm, the core 36a has about 200 µm diameter. It is understood that also significantly different fiber diameters are applicable. The sensing layer 24a comprises a film of an alloy, wherein the alloy of the sensing layer 24a may have compositions which were described above with respect to FIG. 1 to FIG. 4. The catalyst layer 26a typically comprises Pd or a Pd alloy. The catalyst layer 26a is coated with a coating layer 28a. The coating layer typically comprises PMMA and/or PTFE and/or $SiO_2$ and/or Aluminium Oxide, such as $Al_2O_3$. Also, the coating layer 28a may have a multilayer structure itself, comprising at least two or more layers of PMMA, PTFE, $SiO_2$ and Aluminium Oxide. It protects the catalyst layer 26a and sensing layer 24a from the oil or sensor poisonous components in the fluid 12, hence unwanted gases dissolved in the fluid 12 are blocked and hindered from reaching the sensing layer 24a, such as CO or $H_2S$. PTFE may in embodiments be chosen as the outermost coating layer (if several coating layers 28a are present) in order to shield from oil components.

The optical sensor 11a of FIG. 5 typically comprises an auxiliary layer 32a between the catalyst layer 26a and the sensing layer 24a, which abuts the sensing layer 24a. The auxiliary layer 30a preferably comprises Ti, which is suitable to block atoms from either neighbouring layer to diffuse into the respective other layer. A further auxiliary layer 30, also typically comprising Ti, is provided as an adhesive layer between the core 36 of the optical fiber 15a and the sensing layer 24. In embodiments, the coating layer reaches over the entire multilayer 20, that is, also over the circumferential side faces of the multilayer 20 (not shown).

In embodiments, the multilayer 20a is provided on an end surface 17a of the optical fiber 15a, perpendicular to the longitudinal axis of the optical fiber 15a. With other words, the multilayer 20a is provided on the end surface 17a, perpendicular to the optical axis of the optical fiber 15a.

In some embodiments, most or all layers of the multilayer 20a may overlap over the edge 22a of the core 36a to cover a portion of the circumferential side face 34a of the core 36a of the optical fiber 15a.

The second optical sensor 11b, which is not shown in FIG. 5, has typically basically the same structure as the optical sensor 11a shown, wherein in all denominators with an "a" this is replaced by a "b"—hence, the second optical sensor 11b has a second optical fiber 15b, with a second multilayer 20b having a second sensing layer 24b, and so on, but is typically immersed in the same fluid 12 and part of the same optical sensing system 10.

In all embodiments, typical dimensions (i.e., a thickness parallel to the longitudinal axis of the optical fiber) for the varying layers of the multilayer 20a, 20b are: Auxiliary layers 30a, 30b, 32a, 32b, from 2 to 7 nm, more typically from 4 to 6 nm, for example 5 nm. The sensing layer 24a, 24b is typically from 30 to 80 nm, more typically from 40 to 70 nm, for example 60 nm thick. The catalyst layer 26a, 26b is typically from 15 nm to 50 nm, more typically from 20 to 40 nm, for example 30 nm thick. The thickness of the coating layer 28a, 28b may vary depending on its individual setup, in particular if it comprises several layers of differing materials, as described herein. It may thus have a thickness from 3 nm to 5 µm, more typically from 20 nm to 3 µm, for example 1 µm or 2 µm. It shall also be noted that the proportions in the figures are not to scale. For example, the optical fiber 15a in FIG. 5 has a diameter of about 230 µm, whereas the individual layers are in the range from a few nm up to a few μm, as just described. Thus, their height or thickness (in a vertical direction in the drawing plane) is significantly smaller, in reality, in relation to the horizontal dimension of the optical fiber 15a, 15b.

As was laid out above, the optical sensors 11a, 11b exhibit a substantially continuous change, typically decrease, of their optical reflectivity in the visible optical range when exposed to a growing hydrogen concentration (measured in ppm) in a fluid 12 in contact with the optical sensor 11a, 11b. For suitable sensing layers according to embodiments, the optical sensors 11a, 11b show a continuous dependency of their optical reflectance from the hydrogen concentration in a range from about 0° C. to 150° C., more typically form 10° C. to about 100° C., and for hydrogen concentrations in the fluid from about 0.5 ppm to about 5000 ppm, more typically from about 1 ppm to about 1000 ppm.

Figure 6:
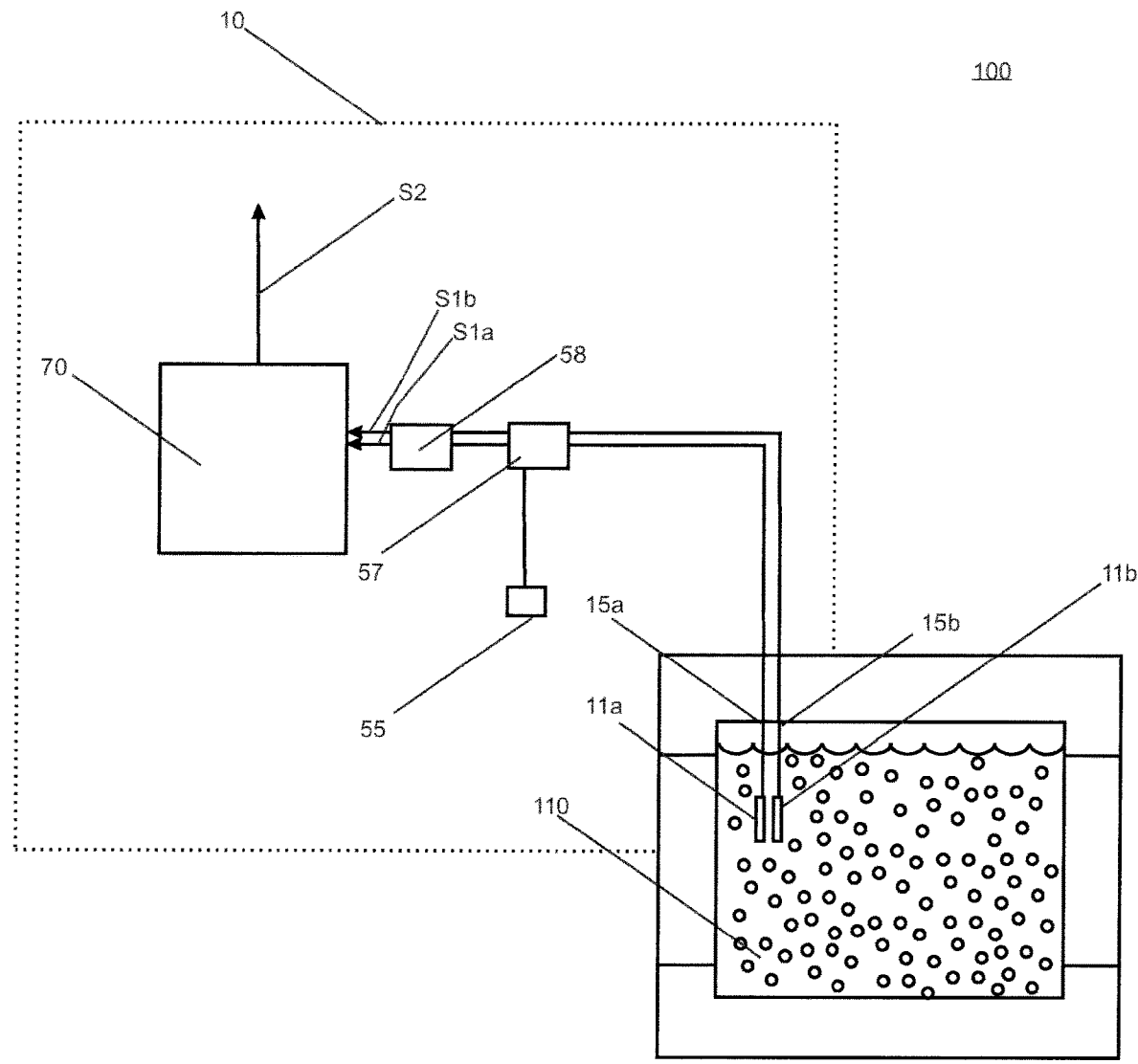
FIG. 6 is a schematic view of an electrical device with an optical sensing system according to embodiments.

The optical sensing systems 10 according to embodiments and the described method can be advantageously employed in electrical devices 100 for electric power generation, transmission, or distribution, which comprise an oil volume 110. In FIG. 6, an electrical device 100 is shown.

It includes an optical sensing system 10 for hydrogen as described for example with respect to FIG. 1. The device 100 is generally a device for electric power generation, transmission, or distribution, and more typically a power transformer or distribution transformer. It comprises an oil volume 110 for insulation and cooling purposes, in which the optical sensors 11a, 11b are immersed. More precisely, the end portions 18a, 18b, with the multilayers 20a, 20b, of the optical fibers 15a, 15b are immersed in the oil volume 110. The oil is one example of the fluid 12 shown in other figures herein.

Although specific features of various embodiments of the invention may be shown in some drawings and not in others, this is for convenience only. In accordance with the principles of the invention, any feature of a drawing may be referenced and/or claimed in combination with any feature of any other drawing.

This written description uses examples to disclose the invention, including the best mode, and also to enable any person skilled in the art to practice the invention, including making and using any devices or systems and performing any incorporated methods. While various specific embodiments have been disclosed in the foregoing, those skilled in the art will recognize that the spirit and scope of the claims allows for equally effective modifications. Especially, mutually non-exclusive features of the embodiments described above may be combined with each other. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

The invention claimed is:

1. An optical sensing system for sensing hydrogen in a fluid, adapted for employing measurement values of at least two differing optical sensors, comprising:
a first optical sensor comprising a first optical fiber, wherein an end portion of the first optical fiber is coated with a first multilayer on an end surface perpendicular to a longitudinal axis of the first optical fiber, the first multilayer being adapted to change its optical reflectance, dependent on a temperature of the fluid, with a known first characteristic being a first parameter matrix of isobars of hydrogen partial pressure, temperature and optical reflectance;
a second optical sensor comprising a second optical fiber, wherein an end portion of the second optical fiber is coated with a second multilayer on an end surface perpendicular to the longitudinal axis of the second optical fiber, the second multilayer being adapted to change its optical reflectance, dependent on the hydrogen partial pressure in the fluid and dependent on a temperature of the fluid, with a known second characteristic being a second parameter matrix of isobars of hydrogen partial pressure, temperature and optical reflectance, which is different from the first characteristic;
at least one light source adapted for coupling light into the first optical fiber and the second optical fiber,
at least one light detector adapted for detecting a light intensity reflected by the first multilayer and a light intensity reflected by the second multilayer,
a control unit operably coupled to the at least one light detector, adapted to calculate the hydrogen partial pressure in the fluid by using the detected light intensity reflected from the first multilayer and the detected light intensity reflected from the second multilayer to determine, from the first parameter matrix and the second parameter matrix, for which hydrogen partial pressure there is a fit in both the first parameter matrix and the second parameter matrix,
wherein the first multilayer comprises a first sensing layer and the second multilayer comprises a second sensing layer, and wherein at least one of the first and second sensing layers comprises a metal alloy comprising $Mg_xNi_yM_z$, wherein M is at least one of Zr, Ta, and Hf, and wherein x is from 40 to 60, y is from 10 to 40, and z is from 10 to 40.

2. The optical sensing system of claim 1, wherein the first sensing layer and the second sensing layer are both hydrogen-sensitive, and wherein the first sensing layer and the second sensing layer exhibit different optical reflectance represented for each of the sensing layers by an individual parameter matrix of isobars of hydrogen partial pressure, temperature and optical reflectance, when exposed to a hydrogen partial pressure in a temperature range from 10° C. to 100° C. and a hydrogen partial pressure range from 10 ppm to 1000 ppm.

3. The optical sensing system of claim 2, wherein the difference of the optical reflectance includes that the slopes of the isobars of hydrogen partial pressure, temperature and optical reflectance are different between the first sensing layer and the second sensing layer by a predefined percentage, over the temperature range and the hydrogen partial pressure range, so that the difference enables the control unit to determine a hydrogen partial pressure in the fluid and/or the temperature of the fluid by employing looked-up values, for each of the first sensing layer and the second sensing layer individually, from the individual parameter matrices of isobars for the conjunction between hydrogen partial pressure, temperature and optical reflectance.

4. The optical sensing system of claim 3, wherein the individual parameter matrices of isobars of hydrogen partial pressure and optical reflectance of the first optical sensor and the second optical sensor are stored in a memory of the control unit.

5. The optical sensing system of claim 2, wherein the individual parameter matrices of isobars of hydrogen partial pressure and optical reflectance of the first optical sensor and the second optical sensor are stored in a memory of the control unit.

6. The optical sensing system of claim 1, wherein the first sensing layer of the first multilayer of the first optical sensor, and the second sensing layer of the second multilayer of the second optical sensor have at least one of the following properties:
  a) the sensing layers comprise materials having a different chemical composition with respect to each other, or b) the sensing layers comprise materials having basically the same chemical composition, but expose different optical reflectance when they are exposed to the same hydrogen partial pressure due to their physical structure, in particular with respect to their internal crystal structure and/or their degree of amorphousness.

7. The optical sensing system of claim 1, wherein the first sensing layer and the second sensing layer each comprise a metal alloy.

8. The optical sensing system of claim 1, wherein at least one of the first and second sensing layers comprises at least one of $Mg_{52}Ni_{20}Zr_{28}$, $Mg_{52}Ni_{24}Zr_{24}$, and $Mg_{55}Ni_{27}Ta_{18}$.

9. The optical sensing system of claim 1, wherein the hydrogen-sensitive multilayers further comprise a catalyst layer and a coating layer, wherein the first or second sensing layers may optionally also be the catalyst layer.

10. The optical sensing system of claim 9, wherein the coating layer comprises PMMA and/or PTFE and/or $SiO_2$ and/or Aluminum Oxide, or has a multilayer structure comprising at least two of PMMA, PTFE, $SiO_2$ and Aluminum Oxide.

11. A method for sensing hydrogen in a fluid, comprising:
  a. providing an optical sensing system comprising:
    a first optical sensor comprising a first optical fiber, wherein an end portion of the first optical fiber is coated with a first multilayer on an end surface perpendicular to a longitudinal axis of the first optical fiber, the first multilayer being adapted to change its optical reflectance, dependent on a hydrogen partial pressure in the fluid and dependent on a temperature of the fluid, with known first characteristic being a first parameter matrix of isobars of hydrogen partial pressure, temperature and optical reflectance;
    a second optical sensor comprising a second optical fiber, wherein an end portion of the second optical fiber is coated with a second multilayer on an end surface perpendicular to the longitudinal axis of the second optical fiber, the second multilayer being adapted to change its optical reflectance, dependent on the hydrogen partial pressure in the fluid and dependent on a temperature of the fluid, with a known second characteristic being a second parameter matrix of isobars of hydrogen partial pressure, temperature and optical reflectance, which is different from the first characteristic;
    at least one light source adapted for coupling light into the first optical fiber and the second optical fiber,
    at least one light detector adapted for detecting a light intensity reflected by the first multilayer and a light intensity reflected by the second multilayer,
    a control unit operably coupled to the at least one light detector, adapted to calculate the hydrogen partial pressure in the fluid by using the detected light intensity reflected from the first multilayer and the detected light intensity reflected from the second multilayer to determine, from the first parameter matrix and the second parameter matrix, for which hydrogen partial pressure there is a fit in both the first parameter matrix and the second parameter matrix,
  b. locating the first optical sensor and the second optical sensor in the fluid in which the hydrogen shall be sensed,
  c. coupling light from at least one light source into the first optical sensor and the second optical sensor,
  d. detecting light reflected from the first optical sensor and the second optical sensor,
  e. calculating, from the intensity of the reflected light from the first multilayer of the first optical sensor and the second multilayer of the second optical sensor, the hydrogen partial pressure in the fluid, using the detected light intensity reflected from the first multilayer and the detected light intensity reflected from the second multilayer to determine, from the first parameter matrix and the second parameter matrix, for which hydrogen partial pressure there is a fit in both the first parameter matrix and the second parameter matrix,
  wherein the first multilayer comprises a first sensing layer and the second multilayer comprises a second sensing layer, and wherein at least one of the first and second sensing layers comprises a metal alloy comprising $Mg_xNi_yM_z$, wherein M is at least one of Zr, Ta, and Hf, and wherein x is from 40 to 60, y is from 10 to 40, and z is from 10 to 40.

12. The method according to claim 11, wherein the difference, between the at least two optical sensors, of stored parameter matrices of isobars of hydrogen partial pressure, temperature and optical reflectance is employed in the determination.

13. A device for electric power generation, transmission, or distribution, comprising:
  an oil volume, and
  an optical sensing system for sensing hydrogen in a fluid, comprising:
    a first optical sensor comprising a first optical fiber, wherein an end portion of the first optical fiber is coated with a first multilayer on an end surface perpendicular to a longitudinal axis of the first optical fiber, the first multilayer adapted to change its optical reflectance, dependent on a hydrogen partial pressure in the fluid and dependent on a temperature of the fluid, with a known first characteristic being a first parameter matrix of isobars of hydrogen partial pressure, temperature and optical reflectance;
    a second optical sensor comprising a second optical fiber, wherein an end portion of the second optical fiber is coated with a second multilayer on an end surface perpendicular to the longitudinal axis of the second optical fiber, the second multilayer adapted to change its optical reflectance, dependent on the hydrogen partial pressure in the fluid and dependent on a temperature of the fluid, with a known second characteristic being a second parameter matrix of isobars of hydrogen partial pressure, temperature and optical reflectance, which is different from the first characteristic;
    at least one light source configured for coupling light into the first optical fiber and the second optical fiber,
    at least one light detector adapted for detecting a light intensity reflected by the first multilayer and a light intensity reflected by the second multilayer,
    a control unit operably coupled to the at least one light detector, adapted to calculate the hydrogen partial pressure in the fluid by using the detected light intensity reflected from the first multilayer and the detected light intensity reflected from the second multilayer to determine, from the first parameter matrix and the second parameter matrix, for which hydrogen partial pressure there is a fit in both the first parameter matrix and the second parameter matrix, wherein the first multilayer comprises a first sensing layer and the second multilayer comprises a second sensing layer, and wherein at least one of the first and second sensing layers comprises a metal alloy comprising Mg$_x$Ni$_y$M$_z$, wherein M is at least one of Zr, Ta, and Hf, and wherein x is from 40 to 60, y is from 10 to 40, and z is from 10 to 40.

* * * * *